United States Patent [19]

Hechtl et al.

[11] Patent Number: 4,462,936
[45] Date of Patent: Jul. 31, 1984

[54] REACTION PRODUCTS OF SILICIC ACID ESTERS AND ORGANIC TIN COMPOUNDS

[75] Inventors: Wolfgang Hechtl, Burghausen; Arnold Garhammer, Simbach, both of Fed. Rep. of Germany

[73] Assignee: Wacker-Chemie GmbH, Munich, Fed. Rep. of Germany

[21] Appl. No.: 400,568

[22] Filed: Jul. 22, 1982

Related U.S. Application Data

[62] Division of Ser. No. 295,961, Aug. 25, 1981, Pat. No. 4,360,654.

[51] Int. Cl.³ .................................................. C07F 7/22
[52] U.S. Cl. ................................... 260/429.7; 528/18
[58] Field of Search ...................................... 260/429.7

[56] References Cited

U.S. PATENT DOCUMENTS

| | | | |
|---|---|---|---|
| 3,384,648 | 5/1968 | Itoi .................................... | 260/429.7 |
| 4,102,860 | 7/1978 | Wohlfarth et al. ........... | 260/429.7 X |
| 4,137,249 | 1/1979 | Wohlfarth et al. ............... | 260/429.7 |
| 4,298,543 | 11/1981 | Law et al. .......................... | 260/429.7 |

*Primary Examiner*—Helen M. S. Sneed

[57] ABSTRACT

Hydroxyl terminated diorganopolysiloxanes may be crosslinked with a mixture containing (1) a product obtained from the reaction of (a) silicic acid esters with (b) an organic tin compound of the formula $$R_2Sn(OCOR^1)_2 \qquad (I),$$

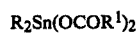

where R represents a butyl or an octyl radical and $R^1$ represents a monovalent hydrocarbon radical having from 1 to 15 carbon atoms, in which at most one of the valences of the carbon atom that is bonded to the carboxyl group is saturated by a carbon atom other than that of the carboxyl group, and (2) an organic tin compound of the formula $$R_2Sn(OCOR^2)_2 \qquad (II),$$

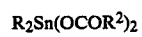

where R is the same as above and $R^2$ represents a monovalent aliphatic hydrocarbon radical having from 3 to 15 carbon atoms, in which at least two of the valences of the carbon atom that is bonded to the carboxyl group are saturated by two carbon atoms other than that of the carboxyl group.

4 Claims, No Drawings

REACTION PRODUCTS OF SILICIC ACID ESTERS AND ORGANIC TIN COMPOUNDS

This is a division of application Ser. No. 295,961, filed Aug. 25, 1981, now U.S. Pat. No. 4,360,654.

The present invention relates to silicon-tin compounds and more particularly to silicon-tin compounds that are obtained from the reaction of silicic acid esters and organic tin compounds and their use as crosslinking agents for organopolysiloxane compositions.

BACKGROUND OF THE INVENTION

Compositions obtained from the reaction of silicic acid esters such as tetraethyl orthosilicate, and organic tin compounds such as dibutyltin dilaurate and their use as crosslinking agents for organopolysiloxane compositions to form elastomers are described in German Pat. No. 1,167,527 to Farbenfabriken Bayer Aktiengesellschaft. U.S. Pat. No. 3,186,963 to Lewis also discloses a catalyst system for vulcanizing silicone elastomer stocks at room temperature in which the catalyst is prepared by heating for at least 15 minutes at a temperature of from 80° to 200° C. a tin salt of a carboxylic acid and an alkylsilicate or partial hydrolysis products of said silicates.

U.S. Pat. No. 3,927,052 to Vizurraga discloses a polymerization catalyst for preparing polyesters which is obtained from the reaction of a first silicon compound of the formula

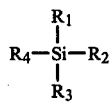

with a second compound of the formula

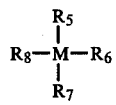

in a mole ratio of from 1.1 to 20 moles of the second compound per mole of the first compound for from two to six hours, in which M may represent a tin atom, $R_2$ and $R_4$ are chlorine or hydroxy groups and the other R substituents are selected from the group consisting of alkyl, acyl, alkoxy, aryloxy, and hydrogen, provided that at least one of $R_5$, $R_6$, $R_7$ and $R_8$ is not hydrogen.

Another reference which discloses silicon-tin compounds as condensation catalysts in the preparation of organopolysiloxane elastomers is U.S. Pat. No. 4,137,249 to Wohlfarth et al in which the silicon-tin compounds are prepared by reacting a silane of the formula $R_aSi(OR^4)_{4-a}$ with a dialkyltin salt of the formula

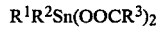

wherein R represents an alkyl or phenyl radical, $R^1$, $R^2$ and $R^3$ are alkyl radicals, $R^4$ is a monovalent hydrocarbon radical, a is 0 or 1 in a molar ratio of $(4-a)$ moles of dialkyltin salt per mole of silane at a temperature of from 50° to 160° C., while removing from 80 to 100 percent of the theoretical amount of by-product ester formed from the reaction.

The products obtained from the reaction of silicic acid esters and an organic tin compound of this invention have certain advantages over the silicon-tin compounds described in the prior art in crosslinking diorganopolysiloxane-based compositions to form elastomers. For example, diorganopolysiloxane based compositions containing the product obtained from the reaction of a silicic acid ester and an organic tin compound can be crosslinked much more rapidly without decreasing the pot-life of the composition. Moreover, the crosslinking agents obtained from the reaction of silicic acid esters and an organic tin compound may be stored at room temperature or heated to a temperature up to 60° C. without a substantial decrease in the crosslinking rate or without substantially altering the pot-life.

Therefore, it is one of the objects of this invention to provide a crosslinking agent for organopolysiloxane compositions. Another object of this invention is to provide a crosslinking agent for room temperature vulcanizable diorganopolysiloxane-based compositions. Still another object of this invention is to provide a crosslinking agent which is obtained from the reaction of a silicic acid ester and an organic tin compound. A further object of this invention is to provide a crosslinking agent which may be heated up to about 60° C. without decreasing the rate of crosslinking or the pot-life.

SUMMARY OF THE INVENTION

The foregoing objects and others which will become apparent from the following description are accomplished in accordance with this invention, generally speaking, by providing crosslinking agents which may be combined with hydroxyl containing diorganopolysiloxanes to form organopolysiloxane elastomers comprising a mixture of (1) a product obtained from the reaction of (a) silicic acid esters and (b) an organic tin compound of the formula

wherein R represents a butyl or an octyl radical and $R^1$ represents a monovalent hydrocarbon radical having from 1 to 15 carbon atoms, in which no more than one of the valences of the carbon atom bonded to the carboxyl group is saturated by a carbon atom other than that of the carboxyl group, and (2) an organic tin compound of the following formula

wherein R is the same as above and $R_2$ represents a monovalent aliphatic hydrocarbon radical having from 3 to 15 carbon atoms, in which at least two of the valences of the carbon atom bonded to the carboxyl group are saturated by at least two carbon atoms other than that of the carboxyl group.

DETAILED DESCRIPTION OF THE INVENTION

The crosslinking agents of this invention are preferably prepared by reacting any monomer, dimer or polymer of silicic acid esters with an organic tin compound of formula (I). Examples of preferred silicic acid esters are silicic acid ethyl esters or silicic acid 2-methoxyethyl esters. Other examples of silicic acid esters are tetraethyl silicate, hexaethoxydisiloxane and ethoxypolysiloxane having an $SiO_2$ content of about 40 percent by weight, also known as "ethylsilicate 40", as well as tetra(2-methoxyethyl)-silicate.

In preparing the reaction products of silicic acid esters and an organic tin compound represented by formula (I), it is possible to use a single silicic acid ester or a mixture of two or more different types of silicic acid esters, for example a mixture consisting of tetraethyl orthosilicate and hexaethoxydisiloxane.

It is preferred that the silicic acid ethyl ester be used in an amount of from 2 to 6 parts by weight for each part by weight of the organic tin compound of formula (I). The radicals represented by R in formula (I) may be the same or different. Also in formula (II), the R radicals may be the same or different. Moreover, the R radicals in the organic tin compound represented by formula (II) may be the same or different from the R radicals in the organic tin compound of formula (I).

The radicals represented by $R^1$ in the organic tin compound of formula (I) may be the same or different. The $R^2$ radicals in the organic tin compound of formula (II) may also be the same or different.

The butyl radicals as well as the octyl radicals may be any isomers such as the n-butyl, sec-butyl, tert-butyl, n-octyl and the 2-ethylhexyl radical.

Examples of preferred organic tin compounds represented by formula (I) are di-n-butyltin diacetate, di-n-octyltin diacetate, di-n-butyltin dilaurate and di-n-octyltin dilaurate.

In preparing the reaction products of silicic acid esters and an organic tin compound represented by formula (I), it is possible to use a single organic tin compound or a mixture of two or more such tin compounds.

The reaction products of the silicic acid esters and an organic tin compound represented by formula (I) are prepared by heating a mixture containing a silicic acid ester and an organic tin compound to a temperature of from 50° to 200° C. for from 15 minutes up to 15 hours.

Examples of carboxylic acids from which the —OCOR$^2$ groups in the organic tin compounds represented by formula (II) are derived, are alkane acids which are mono- or di-substituted in the alpha-position relative to the carboxyl group. Preferred examples of such alkane acids are 2-ethyl-hexanoic acid, so-called KOCH acids which consist of a mixture of carboxylic acids having from 9 to 15 carbon atoms per molecule in which in 90 percent by weight of the acids the carboxyl group is bonded to a tertiary carbon atom, and 2,2,4,4-tetramethyl-1-pentanoic acid. Another acid which may be used is, for example, cyclohexanemonocarboxylic acid.

Examples of preferred organic tin compounds represented by formula (II) are di-n-butyltin diacylate, where the acylate groups are derived from a mixture of carboxylic acids having from 9 to 15 carbon atoms per molecule, in which in 90 percent by weight of the acids the carboxyl group is bonded to a tertiary carbon atom; a di-n-octyltin diacylate where the acylate groups are derived from a mixture of carboxylic acids having from 9 to 15 carbon atoms per molecule, in which in 90 percent by weight of the acids the carboxyl group is bonded to a tertiary carbon atom; di-n-butyltin di-2-ethylhexoate and di-n-octyltin di-2-ethylhexoate.

A single organic tin compound represented by formula (II) or a mixture containing two or more of such organic tin compounds may be combined with the reaction product obtained from the reaction of a silicic acid ester and an organic tin compound represented by formula (I).

The tin compound represented by formula (II) is preferably present in an amount of from 0.1 to 0.2 mole per mole of the tin compound represented by formula (I) which was used in the preparation of the reaction product of a silicic acid ester and an organic tin compound of formula (I).

It is preferred that the organic tin compound of formula (II) be combined with the reaction product of the silicic acid ester and the organic tin compound represented by formula (I) at least during some of the time the reaction product is being stored. However, the organic tin compound represented by formula (II) may be added to the reaction product only shortly prior to its use.

In addition to the product obtained from the reaction of a silicic acid ester and an organic tin compound of formula (I) and an organic tin compound of formula (II), the mixtures of this invention may also contain additional substances such as excess silicic acid esters, hydrophobic silicon dioxide having a surface area of at least 20 m$^2$/g, emollients, soluble dyes and fragrances.

Another embodiment of this invention is a process for preparing organopolysiloxane elastomers which comprises mixing a hydroxyl terminated diorganopolysiloxane composition with a mixture containing (1) a product obtained from the reaction of (a) a silicic acid ester and (b) an organic tin compound of the formula $$R_2Sn(OCOR^1)_2 \qquad (I),$$

wherein R represents a butyl or an octyl radical and $R^1$ is the same or different and represents monovalent hydrocarbon radicals having from 1 to 15 carbon atoms, in which no more than one of the valences of the carbon atom bonded to the carboxyl group is saturated by a carbon atom other than that of the carboxyl group, and (2) an organic tin compound of the formula $$R_2Sn(OCOR^2)_2 \qquad (II),$$

wherein R is the same as above, $R^2$ is the same or different and represents monovalent aliphatic hydrocarbon radicals having from 3 to 15 carbon atoms, in which at least two of the valences of the carbon atom bonded to the carboxyl group are saturated by at least two carbon radicals other than those of the carboxyl group.

The same hydroxyl terminated diorganopolysiloxanes which have been or could have been used heretofore in the preparation of organopolysiloxane elastomers from diorganopolysiloxanes containing Si-bonded hydroxyl groups, a condensation catalyst and a silicon compound having at least three condensable groups per molecule, may be used in the compositions of this invention. In the present invention, the reaction product consisting of a silicic acid ethyl ester and an organic tin compound of formula (I) is to be considered as a combination of a condensation catalyst with a silicon compound containing at least three condensable groups per molecule. These organopolysiloxanes may be represented by the following general formula:

$$HOR_2^3SiO(SiR_2^3O)_xSiR_2^3OH$$
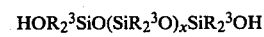

in which $R^3$ represents the same or different, monovalent hydrocarbon radicals or substituted monovalent hydrocarbon radicals and/or polymeric hydrocarbon radicals and x represents an integer having a value of at least 1.

Although this is generally not indicated in the above formula, siloxane units other than diorganosiloxane units ($SiR_2{}^3O$) may be present within or along the siloxane chain. Examples of such other siloxane units which are generally present more or less as impurities, are those having the formulas $R^3SiO_{3/2}$, $R_3{}^3SiO_{1/2}$ and $SiO_{4/2}$, where $R^3$ is the same as above. If such other siloxane units are present, it is preferred that they be present in an amount less than 1 mole percent.

Examples of hydrocarbon radicals represented by $R^3$ are alkyl radicals such as methyl, ethyl, propyl, butyl, hexyl and octyl radicals; alkenyl radicals such as vinyl, allyl, ethylallyl and the butadienyl radical; as well as aryl radicals such as the phenyl radical.

Examples of substituted hydrocarbon radicals represented by $R^3$ are halogenated hydrocarbon radicals such as the 3,3,3-trifluoropropyl radical, chlorophenyl and bromotolyl radicals; as well as the cyanoalkyl radicals, such as the beta-cyanoethyl radical.

Also, $R^3$ represents substituted and unsubstituted polymeric hydrocarbon radicals and/or copolymers which are bonded to silicon via carbon. These polymeric radicals or copolymers are obtained from the polymerization of at least one polymerizable monomer containing a carbon-carbon double bond, such as ethylene, styrene, vinylacetate, n-butylacrylate, n-butylmethacrylate or acrylonitrile. Siloxanes containing polymeric hydrocarbon radicals are referred to as modified organopolysiloxanes.

Because they are readily available, it is preferred that at least 80 percent of the number of $R^3$ radicals be methyl radicals. Other radicals represented by $R^3$ are preferably vinyl and/or phenyl radicals.

The viscosity of the diorganopolysiloxanes used in the process of this invention is generally from 100 to $10^6$ mPa.s at 25° C.

Mixtures of various diorganopolysiloxanes may likewise be employed.

In preparing organopolysiloxane elastomers, a mixture consisting of (1) the product obtained from the reaction of (a) a silicic acid ester and (b) an organic tin compound represented by formula (I) and (2) an organic tin compound represented by formula (II), is mixed with a hydroxyl-terminated diorganopolysiloxane in an amount of from 2 to 10 percent by weight, based on the weight of the diorganopolysiloxane to be crosslinked.

In addition to the hydroxyl-terminated diorganopolysiloxane and the crosslinking agents of this invention, the compositions may also include other substances that have been or could have been employed heretofore in organopolysiloxane compositions which may be crosslinked to form elastomers. Examples of such other substances are reinforcing and non-reinforcing fillers, such as pyrogenically produced silicon dioxide, diatomaceous earth, quartz meal, gypsum, precipitated calcium sulfate, aluminum silicate as well as polyvinyl chloride powder, pigments, water, soluble dyes, fragrances, corrosion-inhibitors, emollients such as trimethylsiloxy endblocked dimethylpolysiloxanes which are liquid at room temperature, polyglycols which may be etherified and/or esterified, and agents which serve to improve the adhesion of the organopolysiloxane elastomers to the bases on which they are applied, such as epoxyalkylsilanes, as well as solvents.

In the process of this invention, the hydroxyl-terminated diorganopolysiloxane, the crosslinking agent and any other substances which are generally present in organopolysiloxanes which are cured to elastomers are preferably mixed at temperatures of from about $-5°$ up to about 40° C., and under atmospheric pressure. However, higher or lower temperatures and pressures may also be used.

Compositions of this invention are particularly useful in the preparation of impressions, especially dental impressions, as well as for the preparation of molded objects and coatings.

In the following examples, all parts and percentages are by weight, unless otherwise specified.

EXAMPLE 1

(a) A mixture containing 3 parts of an ethoxypolysiloxane having an $SiO_2$ content of about 40 percent and 1 part di-n-butyltin dilaurate (formula I) was heated for 12 hours at 120° C. The product obtained from the reaction of the silicic acid ethyl ester and the dibutyltin dilaurate was cooled and mixed with 5 percent by weight of di-n-butyltin diacylate (formula II) in which the acylate groups were derived from a mixture of carboxylic acids containing from 9 to 15 carbon atoms per molecule, in which in 90 percent of the acids, the carboxyl groups are bonded to a tertiary carbon atom ("dibutyltin diversatate").

Immediately after its preparation, and again after storing for six months at room temperature, the mixture obtained in accordance with this invention was incorporated in an organopolysiloxane-filler mixture consisting of:

510 g of an Si-bonded hydroxyl terminated dimethylpolysiloxane having a viscosity of 12,000 mPa.s at 23° C.;

510 g of an Si-bonded hydroxyl terminated dimethylpolysiloxane having a viscosity of 1,000 mPa.s at 23° C.;

162 g of a trimethylsiloxy terminated dimethylpolysiloxane having a viscosity of 100 mPa.s at 23° C.; and 690 g quartz meal at the rate of 3 percent by weight based on the weight of the organopolysiloxane and filler mixture. The organopolysiloxane-filler mixture had been mixed with 0.3 percent by weight of water, based on the weight of the mixture, and stored for 3 days at room temperature prior to the addition of the silicic acid ethyl ester-organic tin mixture prepared above. The crosslinking behavior of this mixture was observed at 23° C. and at 50 percent relative humidity. The results are shown in Table 1.

EXAMPLE 2

The procedure described in Example 1 is repeated, except that 5 percent by weight of di-n-butyltin di-2-ethylhexoate was substituted for the di-n-butyltin diacylate.

EXAMPLE 3

The procedure described in Example 1 was repeated, except that 5 percent by weight of di-n-octyltin di-2-ethylhexoate was substituted for the di-n-butyltin diacylate.

COMPARISON EXAMPLE (a)

The procedure described in Example 1 was repeated, except that no tin compound was added to the reaction product of ethoxypolysiloxane and di-n-butyltin dilaurate. The reaction product was used at the rate of 5 percent by weight based on the total weight of the organopolysiloxane and the filler.

COMPARISON EXAMPLE (b)

The procedure described in Example 1 was repeated, except that 5 percent by weight of di-n-butyltin diacetate, (formula I) was added to the reaction product of ethoxypolysiloxane and di-n-butyltin dilaurate.

EXAMPLE 4

A mixture consisting of 3 parts ethoxypolysiloxane having an $SiO_2$ content of about 40 percent and one part of di-n-butyltin diacetate (formula I) was heated under reflux for 6 hours at a bath temperature of 105° C. The product obtained from the reaction of a silicic acid ethyl ester and the organic tin compound of formula (I) was cooled and then mixed with 5 percent by weight of the di-n-butyltin diacylate of formula (II) ("dibutyltindiversatate") described in Example 1. The resultant mixture was then added immediately after its preparation and again after storing for 6 months at room temperature to an organopolysiloxane-filler composition consisting of:
230 g of a dimethylpolysiloxane containing Si-bonded terminal hydroxyl groups and having a viscosity of 20,000 mPa.s at 23° C.;
230 g of a dimethylpolysiloxane containing Si-bonded terminal hydroxyl groups and having a viscosity of 350,000 mPa.s at 23° C.; and
1,420 g precipitated calcium sulfate
at the rate of 0.75 percent based on the total weight of the organopolysiloxane and filler. The organopolysiloxane-filler mixture had been mixed with 0.3 percent by weight of water, based on the weight of the mixture, and stored for 3 days at room temperature prior to the addition of the silicic acid ethyl ester-organic tin mixture prepared above. The crosslinking behavior of the mixture was then observed at 23° C. and at 50 percent relative humidity. The results are shown in Table 2.

EXAMPLE 5

The procedure described in Example 4 was repeated, except that 5 percent by weight of di-n-butyltin di-2-ethylhexoate (formula II), was substituted for the di-n-butyltin diacylate.

EXAMPLE 6

The procedure described in Example 4 was repeated, except that 5 percent by weight of di-n-octyltin di-2-ethylhexoate was substituted for di-n-butyltin diacylate.

COMPARISON EXAMPLE (a')

The procedure described in Example 4 was repeated, except that the only tin compound employed was the reaction product of ethoxypolysiloxane and di-n-butyltin diacetate and the reaction product was employed in an amount of 2 percent by weight based on the total weight of the organopolysiloxane and the filler.

EXAMPLE 7

A mixture containing 3 parts of tetraethyl orthosilicate and 1 part di-n-butyl diacetate (formula I) was heated for 8 hours under reflux at a bath temperature of 105° C. The product obtained from the reaction of the silicic acid ethyl ester and the organic tin compound of formula (I) was cooled and mixed with 5 percent by weight based on the weight of the reaction product of the di-n-butyltin diacylate of formula (II) ("dibutyltindiversatate") described in Example 1. The resultant mixture was then incorporated after its preparation and again after being stored for 6 months at room temperature in an organopolysiloxane-filler composition consisting of:
650 g of a dimethylpolysiloxane containing terminal Si-bonded hydroxyl groups and having a viscosity of 1,000 mPa.s at 23° C., and
350 g diatomaceous earth,
in an amount of 3.2 percent by weight based on the total weight of the organopolysiloxane and filler mixture. The organopolysiloxane-filler mixture was heated to 135° C. for 8 hours to remove the volatile components, cooled, and then 0.2 percent by weight of water was added and stored for 3 days at room temperature prior to the addition of the mixture containing the silicic acid ethyl ester-organic tin compound prepared above. The crosslinking behavior of the mixture was then observed at 23° C. and at 50 percent relative humidity. The results are shown in Table 3.

EXAMPLE 8

The procedure described in Example 7 was repeated, except that 5 percent di-n-octyltin diacylate (formula II) in which the acylate groups were derived from a mixture of carboxylic acids containing from 9 to 15 carbon atoms per molecule, in which in 90 percent of the acids, the carboxyl group was bonded to a tertiary carbon atom (a "dioctyltindiversatate") was substituted for the di-n-butyltin diacylate described in Example 1.

EXAMPLE 9

The procedure of Example 7 was repeated, except that 5 percent by weight of di-n-butyltin di-2-ethylhexoate (formula II) was substituted for the di-n-butyltin diacylate described in Example 1.

EXAMPLE 10

The procedure described in Example 7 was repeated, except that 5 percent by weight of di-n-octyltin di-2-ethylhexoate (formula II) was substituted for the di-n-butyltin diacylate described in Example 1.

COMPARISON EXAMPLE (a")

The procedure described in Example 7 was repeated, except that no tin compound was used except for the product obtained from the reaction of tetraethyl orthosilicate and di-n-butyltin dilaurate and the reaction product was used in an amount of 4 percent by weight based on the total weight of the organopolysiloxane and the filler.

In the following tables the term "processing time" is the period of time which elapses between the time that mixing of components to be crosslinked in the formation of elastomers is initiated, and the time that crosslinking of the components is first observed.

The figures shown in parentheses in the tables were recorded after the mixture containing the reaction product from silicic acid ethyl ester and a tin compound of formula (I) and a tin compound of formula (I or II), had been stored for 6 months. Essentially, the same values were obtained after the mixtures containing the reaction product of silicic acid ethyl ester and a tin compound of formula (I) and a tin compound of formula (II) had been stored for 4 weeks at 60° C., in accordance with Examples 1 to 10.

TABLE 1

| | Processing Time | Shore-A-Hardness after | | | |
| --- | --- | --- | --- | --- | --- |
| | | 10 min. | 15 min. | 30 min. | 24 hours |
| Example | | | | | |
| 1 | 3 min. 20 sec. | 23 | 30 | 32 | 41 |
| | (3 min. 15 sec.) | (23) | (29) | (32) | (40) |
| 2 | 3 min. 15 sec. | 23 | 30 | 31 | 41 |
| | (3 min. 20 sec.) | (22) | (29) | (32) | (41) |
| 3 | 3 min. 20 sec. | 22 | 29 | 31 | 41 |
| | (3 min. 25 sec.) | (21) | (28) | (31) | (41) |
| Comparison Examples | | | | | |
| (a) | 3 min. 50 sec. | 0 | 1 | 5 | 30 |
| (b) | 3 min. 50 sec. | 18 | 28 | 30 | 41 |
| | (5 min. 5 sec.) | (0) | (6) | (19) | (40) |

TABLE 2

| | Processing Time | Shore-A-Hardness after | | | | |
| --- | --- | --- | --- | --- | --- | --- |
| | | 10 min. | 13 min. | 15 min. | 30 min. | 24 hours |
| Example | | | | | | |
| 4 | 3 min. 30 sec. | 28 | 36 | 41 | 44 | 58 |
| | (3 min. 25 sec.) | (29) | (37) | (41) | (42) | (58) |
| 5 | 3 min. 25 sec. | 29 | 37 | 41 | 46 | 58 |
| | (3 min. 20 sec.) | (29) | (39) | (43) | (47) | (58) |
| 6 | 3 min. 30 sec. | 25 | 36 | 39 | 48 | 58 |
| | (3 min. 30 sec.) | (24) | (37) | (42) | (49) | (58) |
| Comparison Example | | | | | | |
| (a') | 4 min. 5 sec. | 4 | 17 | 20 | 39 | 59 |

TABLE 3

| | Processing Time | Shore-A-Hardness after | | | | |
| --- | --- | --- | --- | --- | --- | --- |
| | | 10 min. | 13 min. | 15 min. | 30 min. | 24 hours |
| Example | | | | | | |
| 7 | 4 min. 10 sec. | 41 | 51 | 53 | 56 | 65 |
| | (4 min. 10 sec.) | (41) | (51) | (53) | (56) | (65) |
| 8 | 4 min. 5 sec. | 36 | 49 | 52 | 56 | 65 |
| | (4 min. 5 sec.) | (37) | (48) | (51) | (56) | (65) |
| 9 | 4 min. 5 sec. | 38 | 49 | 53 | 58 | 66 |
| | (4 min. 10 sec.) | (37) | (48) | (53) | (58) | (66) |
| 10 | 4 min. 15 sec. | 35 | 47 | 51 | 56 | 66 |
| | (4 min. 15 sec.) | (35) | (48) | (51) | (57) | (66) |
| Comparison Example | | | | | | |
| (a") | 5 min. | 12 | 27 | 30 | 47 | 63 |

The above tables show that the cross-linking behavior of the compositions of this invention is far less influenced by storage than that of other compositions and that the compositions containing the mixtures of organic tin compounds crosslink more rapidly.

EXAMPLE 11

A mixture containing 3 parts of tetraethyl orthosilicate and 1 part of di-n-octyltin diacetate (formula I) was heated for 3 hours under reflux and at a bath temperature of 120° C. After the bath temperature had cooled to 50° C., the volatile components were distilled off at 50° C. and at 22 mBar (absolute). The product obtained from the reaction of the silicic acid ethyl ester and the organic tin compound of formula (I) was then mixed with 5 percent by weight of di-n-octyltin di-2-ethylhexoate (formula II). The resultant mixture was then mixed with the organopolysiloxane-filler mixture described in Example 4 in an amount of 3.2 percent by weight, based on the total weight of the organopolysiloxane and the filler after the organopolysiloxane-filler mixture had been kneaded with 0.3 percent by weight of water and stored for 3 days at room temperature. The crosslinking behavior of the mixture was observed at 23° C. and at 50 percent relative humidity. The following results were obtained.

| | Shore-A-Hardness after | | | |
| --- | --- | --- | --- | --- |
| Processing Time | 10 min. | 13 min. | 15 min. | 24 hours |
| 3 min. 45 sec. | 35 | 47 | 50 | 65 |

EXAMPLE 12

A mixture containing 3 parts of tetra-(2-methoxyethyl)silicate and 1 part di-n-butyltin dilaurate (formula I) was heated for 3 hours at a bath temperature of 140° C. After it had cooled, the product obtained from the reaction of the silicic acid ester and the organic tin compound of formula (I) was mixed with 5 percent by weight of di-n-butyltin di-2-ethylhexoate (formula II). This mixture was then combined with the organopolysiloxane-filler mixture described in Example 7, at the rate of 2.5 percent, based on the total weight of the organopolysiloxane and filler after the organopolysiloxane-filler mixture had been heated for 8 hours at 135° C. to remove the volatile components, cooled, then mixed with 0.2 percent by weight of water and stored for 3 days at room temperature. The crosslinking behavior of the resultant mixture was observed at 23° C. and at 50 percent relative humidity. The following results were observed.

| | Shore-A-Hardness after | | | |
| --- | --- | --- | --- | --- |
| Processing Time | 8 min. | 10 min. | 15 min. | 24 hours |
| 3 min. 45 sec. | 24 | 35 | 41 | 55 |

COMPARISON TEST

The procedure described in Example 12 was repeated, except that no tin compound was used except for that obtained from the reaction of the silicic acid ester and di-n-butyltin dilaurate. The reaction product was used in an amount of 4 percent by weight based on the total weight of the organopolysiloxane and the filler. The following results were observed:

| | Shore-A-Hardness after | | | |
| --- | --- | --- | --- | --- |
| Processing Time | 8 min. | 10 min. | 15 min. | 24 hours |
| 3 min. 20 sec. | 0 | 11 | 23 | 52 |

What is claimed is:
1. A mixture containing (1) a product obtained from the reaction of (a) silicic acid ester and (b) an organic tin compound of the formula

$$R_2Sn(OCOR^1)_2 \qquad (I),$$

wherein R is selected from the group consisting of a butyl and an octyl radical, $R^1$ is a monovalent hydrocarbon radical having from 1 to 15 carbon atoms, in which only one of the valences of the carbon atom which is bonded to the carboxyl group is saturated by a carbon atom other than that of the carboxyl group and (2) an organic tin compound of the formula $$R_2Sn(OCOR^2)_2 \quad (II),$$

wherein R is selected from the group consisting of a butyl and an octyl radical, $R^2$ is a hydrocarbon radical having from 3 to 15 carbon atoms, in which at least two of the valences of the carbon atom which is bonded to the carboxyl group are saturated by at least two carbon atoms other than those of the carboxyl group.

2. The mixture of claim 1, wherein the organic tin compound represented by formula II is selected from the group consisting of a di-n-butyltin diacylate, in which the acylate groups are derived from a mixture of carboxylic acids having from 9 to 15 carbon atoms per molecule, in which in 90 percent by weight of the acids, the carboxyl group is bonded to a tertiary carbon atom; a di-n-octyltin diacylate wherein the acylate groups are derived from a mixture of carboxylic acids having from 9 to 15 carbon atoms per molecule, in which in 90 percent by weight of the acids, the carboxyl group is bonded to a tertiary carbon atom; di-n-butyltin di-2-ethylhexoate and di-n-octyltin di-2-ethylhexoate.

3. The mixture of claim 1, wherein the silicic acid ester (a) and the organic tin compound of formula I (b) are reacted at a temperature of from 50° to 200° C.

4. The mixture of claim 1, wherein the silicic acid ester (a) is present in an amount of from 2 to 6 parts by weight for each part by weight of the organic tin compound of formula I (b).

* * * * *